(12) United States Patent
Dohi et al.

(10) Patent No.: US 10,414,986 B2
(45) Date of Patent: Sep. 17, 2019

(54) METHOD FOR MANUFACTURING COKE, COKE, AND METHOD FOR EVALUATING HOMOGENEITY OF COAL BLEND

(71) Applicant: JFE STEEL CORPORATION, Tokyo (JP)

(72) Inventors: Yusuke Dohi, Fukuyama (JP); Yoshiko Maeta, Ashikaga (JP); Kazutoshi Hanada, Chiba (JP); Kiyoshi Fukada, Fukuyama (JP); Takashi Matsui, Fukuyama (JP); Michio Honma, Kurashiki (JP); Masahiro Shinohara, Kurashiki (JP)

(73) Assignee: JFE STEEL CORPORATION, Tokyo (JP)

( * ) Notice: Subject to any disclaimer, the term of this patent is extended or adjusted under 35 U.S.C. 154(b) by 148 days.

(21) Appl. No.: 15/312,400

(22) PCT Filed: May 15, 2015

(86) PCT No.: PCT/JP2015/002470
§ 371 (c)(1),
(2) Date: Nov. 18, 2016

(87) PCT Pub. No.: WO2015/177998
PCT Pub. Date: Nov. 26, 2015

(65) Prior Publication Data
US 2017/0218276 A1    Aug. 3, 2017

(30) Foreign Application Priority Data

May 19, 2014    (JP) ................................. 2014-102931

(51) Int. Cl.
*C10B 57/04*    (2006.01)
*C10B 57/10*    (2006.01)
(Continued)

(52) U.S. Cl.
CPC .............. *C10B 57/04* (2013.01); *C10B 41/02* (2013.01); *C10B 53/04* (2013.01); *C10B 57/10* (2013.01); *G01N 33/222* (2013.01)

(58) Field of Classification Search
CPC ......... C10B 57/04; C10B 53/04; C10B 41/02; C10B 57/10; G01N 33/222
See application file for complete search history.

(56) References Cited

U.S. PATENT DOCUMENTS 4,450,046 A * 5/1984 Rice .......................... C10L 9/10
201/20
5,230,211 A * 7/1993 McMahon ............... C02F 11/10
110/346

FOREIGN PATENT DOCUMENTS

CA    2892336 A1 *  5/2014  ............. C10B 53/04
CN    101910364 A    12/2010
(Continued)

OTHER PUBLICATIONS

Apr. 5, 2017 European Search Report issued in European Patent Application No. 15796775.3.
(Continued)

*Primary Examiner* — Brian A McCaig
(74) *Attorney, Agent, or Firm* — Oliff PLC

(57) ABSTRACT

A method for manufacturing coke having a high strength and excellent extrusion capability. The method includes a preparing step of blending two or more coal brands to prepare a coal blend, a stirring and mixing step of stirring and mixing the coal blend to disintegrate at least a part of pseudo-particles that have been formed by agglomeration of coal particles in the coal blend, and a carbonizing step of charging the stirred and mixed coal blend into a coke oven to carbonize the stirred and mixed coal blend. Additionally, a mixing apparatus is used in the stirring and mixing step that has a capability of controlling a degree of mixing of the coal (Continued)

blend to be 0.85 or more at 60 seconds after start of a mixing operation. The degree of mixing is calculated by the following equation (1):

$$\text{degree of mixing} = (\sigma C_0 - \sigma C)/(\sigma C_0 - \sigma C_f) \quad (1).$$

6 Claims, 7 Drawing Sheets

(51) Int. Cl.
  *C10B 53/04* (2006.01)
  *C10B 41/02* (2006.01)
  *G01N 33/22* (2006.01)

(56) References Cited

FOREIGN PATENT DOCUMENTS

| | | |
|---|---|---|
| CN | 102031172 A | 4/2011 |
| EP | 2 233 548 A1 | 9/2010 |
| JP | H02-167394 A | 6/1990 |
| JP | H06-330052 A | 11/1994 |
| JP | 2004-027076 A | 1/2004 |
| JP | 2005-336311 A | 12/2005 |
| JP | 2007-009051 A | 1/2007 |
| JP | 2007-077254 A | 3/2007 |
| JP | 2007-112941 A | 5/2007 |
| WO | 2014/080817 A1 | 5/2014 |

OTHER PUBLICATIONS

J. L. Sundholm et al., "7. Manufacture of Metallurgical Coke and Recovery of Coal Chemicals"; "Ironmaking volume", Jan. 1, 1999, The AISE Steel Foundation, XP055272111, pp. 381-546.
Shatokha I Z et al., "Estimation of degree of mixing (Uniformity) of coal charges"; Coke Chem USSR; Coke and Chemistry, U.S.S.R. 1965 Leeds, England, No. 2, pp. 3-5, XP8183864.
Lazovskii I M et al., "Influence of degree of mixing of coal charges on coke strength"; Coke Chem USSR; Coke and Chemistry, U.S. S.R. 1965 Leeds, England, No. 11, pp. 24-26, XP8183862.
Okoshi et al., "Coke Circular", vol. 20, 1971, p. 271.
Oct. 18, 2017 Office Action issued in Korean Patent Application No. 10-2016-7031708.
P.M.C. Lacey, "The Mixing of Solid Particles", Chemical Engineering Research and Design, vol. 75, Jubilee Supplement, Dec. 1997, pp. S49-S55.
Dec. 12, 2017 Office Action issued in European Patent Application No. 15796775.3.
Jun. 30, 2015 International Search Report issued in International Application No. PCT/JP2015/002470.
Nov. 1, 2018 Office Action issued in Chinese Application No. 201580025269.8.

\* cited by examiner (a)

(b)

METHOD FOR MANUFACTURING COKE, COKE, AND METHOD FOR EVALUATING HOMOGENEITY OF COAL BLEND

TECHNICAL FIELD

The present disclosure relates to a method for manufacturing coke by charging a coal blend into a coke oven and carbonizing the coal blend, coke manufactured by using the method, and a method for evaluating the homogeneity of a coal blend.

BACKGROUND ART

In general, in a coke oven, various kinds of operational problems occur due to the progress of aging. Among such operational problems, "sticker" is a very serious operational problem that it is not possible to discharge manufactured coke from a coke oven. Since "sticker" occurrence forces change in a schedule for manufacturing coke, the amount of produced coke becomes decreasing and the life of the coke oven becomes shortened due to induced damage to the oven body. Therefore, decreasing the frequency of occurrence of "sticker" is given first priority in the operation.

A mechanism by which "sticker" occurs is roughly described as follows. The operation of a general chamber-type coke oven involves carbonizing a coal blend which has been charged into a carbonizing chamber to form a coke cake sequentially from the oven wall side due to heat transferred from a combustion chamber adjacent to the carbonizing chamber. Here, usually, since a coke cake shrinks due to carbonization, a gap (hereinafter, referred to as "clearance") is formed between the oven wall and the outer surface of the coke cake. Formation of the clearance facilitates to discharge (extrude) the coke cake from the coke oven.

However, since an insufficient amount of shrinkage of a coke cake does not form a sufficiently large clearance, "sticker" occurs due to increased frictional resistance between the oven walls and the outer surface of the coke cake when the coke cake is extruded. Also, in the case where irregularity of the oven wall surface is large, "sticker" occurs due to increased frictional resistance between the oven walls and the outer surface of the coke cake. The irregularity of the oven wall surface is increased as a result of the abrasion and removal of oven wall bricks, an increase in the amount of carbon adhered to the oven walls, and so forth due to the aging of the coke oven. Therefore, frequency of occurrence of "sticker" inevitably increases due to the aging of a coke oven. In consideration of such a background, in case of operating of an aging coke oven, various countermeasures are implemented in order to decrease the frequency of occurrence of "sticker".

A moisture-coal operation can be mentioned for an example of countermeasures aimed at decreasing the frequency of occurrence of "sticker". The moisture-coal operation involving using a coal blend of which the moisture content is not actively decreased from the content (about 8 mass % to 14 mass %, although it depends on season and weather) when the coal blend is piled in a coal yard. The moisture-coal operation is widely used as the simplest and effective method. Increasing the moisture content of a coal blend makes the bulk density of a charged coal blend decrease and there is an increase in clearance or the like, thereby reducing frictional resistance between the oven walls and the surface of a coke cake when the coke cake is extruded. At the result thereof, it is possible to decrease the frequency of occurrence of "sticker".

As a specific example of the method described above, Patent Literature 1 discloses a technique involving carbonizing a coal blend in a coke oven after the moisture content of the coal blend has been controlled by a coal-moisture-controlling apparatus. The technique involves determining the target moisture content of a coal blend necessary to achieve desired clearance on the basis of the relationship derived in advance between the moisture content of the coal blend and clearance, and controlling the heat input to a coal-moisture-controlling apparatus so that the total moisture content of the coal blend at the exit of the coal-moisture-controlling apparatus is the target moisture content. Such controlling decreases the frequency of occurrence of "sticker".

In addition, Patent Literature 2 discloses a technique involving adding water locally to a coal in a coal tower and charging the coal into a carbonizing chamber via a larry car. The technique makes clearance increase due to an increase in the shrinkage ratio of coke in a part of the coal having an increased moisture content existing locally in the carbonizing chamber. The increase of clearance results in a decrease in the frequency of occurrence of "sticker".

The conventional techniques described above have a common technical feature. The feature is increasing the moisture content of coal to be charged into a coke oven to form a clearance with an increased shrinkage ratio when carbonization is performed.

On the other hand, a blast furnace operation recently involves blowing pulverized coal into a blast furnace in order to decrease the amount of coke used. The operation needs coke having relatively higher strength, in particular, coke excellent in terms of drum strength which is determined by using a drum strength test method prescribed in JIS K 2151 is necessary. The blast furnace requires sufficient gas permeability and liquid permeability so as to progress the reducing reaction of iron ore efficiently and stably. In case of insufficient coke strength, there occurs a problem of a decrease in gas permeability and liquid permeability in a hollow space called a "raceway" which is formed in front of a tuyere and the lower part of the blast furnace due to the collision of coke particles.

Techniques for improving coke strength are largely classified into three groups in terms of processes in which they are used, that is, pretreatment techniques, blending techniques, and carbonizing techniques. In particular, pretreatment techniques are considered to be important, because the techniques makes it possible to design equipment so that there is no limitation on the productivity of a coke oven without an increase in the costs for coal blend. Such pretreatment techniques are classified mainly into the following two groups in terms of the approach to coke strength.

(1) A technique for improving the charged bulk density of a coal blend (hereinafter, referred to as "technique (1)")

(2) A technique for homogenizing a coal blend (hereinafter, referred to as "technique (2)")

The technique (1) is intended to decrease the number of pore defects which influence coke strength. The technique (1) involves mechanically compacting a coal blend to improve charged bulk density and charging the coal blend into a coke oven so as to reduce the interparticle space of the coal. The technique (1) results in an improvement in coke strength. Specific examples of the technique include a method of charging coal briquettes partially, a stamping method, and a method of decreasing the moisture content of a coal blend in order to decrease the interparticle adhesiveness of the coal to improve the charged bulk density (refer to Non Patent Literature 1). However, a process in which the moisture content of a coal blend is decreased by using a moisture-controlling apparatus or a preheating apparatus is introduced into an operation of many coke ovens.

In contrast, the technique (2) is intended to increase the strength of a portion of coke having the lowest strength. Since coal is fundamentally composed of textures having different properties in terms of various thermal and mechanical properties, coal is very inhomogeneous. Naturally, the structure of coke, which is manufactured from such inhomogeneous coal, is also inhomogeneous. Generally, the strength of a brittle material such as coke is described on the basis of a weakest link model and determined by the strength of a portion having the lowest strength in the material. Therefore, since the strength of coke is homogenized by homogenizing the structure of the coke, the technique (2) makes it possible to improve the strength of the entire coke.

Examples of a method for the technique (2) include a method in which the particle size of coal is controlled (refer to Non Patent Literature 1). The method of controlling the particle size of coal is basically intended to homogenize the structure of coke by finely pulverizing coal. Also, a method is known which is intended to homogenize the structure of coke by treating coal with a coal-mixing machine such as a drum mixer in order to increase the degree of mixing of the coal (refer to Non Patent Literature 2). However, it has been clarified by conventional research that, without being treated with a coal-mixing machine, a coal blend which is used in a coke-making process is sufficiently mixed, for example, at connection parts of a belt conveyer in a transportation process (refer to Non Patent Literature 2). Therefore, in many coke plants, consideration is given to homogenize the structure of coke without using a coal-mixing machine nowadays.

CITATION LIST

Patent Literature

PTL 1: Japanese Unexamined Patent Application Publication No. 2004-27076
PTL 2: Japanese Unexamined Patent Application Publication No. 2007-9051

Non Patent Literature

NPL 1: Sakawa et al., "Coal and Coke", 2002, the Iron and Steel Institute of Japan, Tokyo
NPL 2: Okoshi et al., "Coke Circular", Volume 20, 1971, p. 271
NPL 3: Yamamoto et al., "Current Advances in Materials and Processes", Volume 20, 2007, p. 876

SUMMARY

Technical Problem

In order to stably operate a coke oven and a blast furnace, it is necessary to realize both the achievement of a sufficient clearance due to the shrinkage of a coal blend and the achievement of sufficient coke strength at the same time.

However, since the techniques according to Patent Literature 1 and Patent Literature 2 and techniques (1) and (2) have the following problems, it is a fact that both are not realized at the same time currently.

The technique according to Patent Literature 1 involves controlling the moisture content of a coal blend to control clearance in order to achieve a target clearance which is necessary to inhibit "sticker" from occurring. Therefore, although the technique is effective for inhibiting "sticker" from occurring, it is not possible to inhibit a decrease in coke strength. Also, since the technique according to Patent Literature 2 involves controlling the moisture content of a coal blend to control clearance, it is not possible to inhibit a decrease in coke strength.

In contrast, although the technique (1) is effective for improving coke strength, since there is a decrease in clearance due to an increase in the bulk density of a coal blend, it is not possible to inhibit "sticker" from occurring.

The technique (2) is effective not only for improving coke strength but also for achieving a sufficient clearance (refer to Non Patent Literature 3). However, in the case where the moisture content of a coal blend is high, since coal particles agglomerate through water even if a coal blend is pulverized into a small particle size, large pseudo-particles are formed. The pseudo-particles remain indisintegrated even if the pseudo-particles in the coal blend are subjected to stirring and mixing using a coal-mixing machine such as a drum mixer which mainly involves convective mixing, and therefore it is not possible to achieve sufficient coke strength due to inhomogeneous structure formed inside the coke. In addition, the influence of the behavior and configuration such as size and structure of the pseudo-particles on coke strength has not been sufficiently clarified. Therefore, a preferable method for breaking the pseudo-particles has not been clarified yet.

It is necessary to decrease the moisture content of a coal blend in order to improve coke strength for the reason described above. However, since there is an increase in the frequency of occurrence of "sticker" in the case of low moisture content, there is a trend toward rather increasing the moisture content of a coal blend. It is a fact that currently an aging coke oven which has been used for more than 40 years is operated with the moisture content of a coal blend being maintained at a high level at the sacrifice of coke strength.

On the other hand, in the case where pseudo-particles are disintegrated in order to improve homogeneity, it is not clear what kind of index should be used to evaluate homogeneity or what level of homogeneity should be provided in order to obtain coke having a desired strength.

The present disclosure has been completed in view of the problems described above, and an object of the present disclosure is to provide coke having a high strength and excellent discharging property from a coke oven and a method for manufacturing the coke, and, in addition, to provide a method for quantitatively evaluating the homogeneity of a coal blend.

Solution to Problem

The present inventors, in view of the problems described above, diligently conducted investigations regarding the influence of the homogeneity of a coal blend on coke strength from the viewpoint of pseudo-particles.

As a result, the present inventors found that it is highly probable that the homogeneity on the order of millimeters of a coal blend influences coke strength. The present inventors found that there is a decrease in homogeneity in the case where the number of particles in coal of a single brand (hereinafter, refers to as "single coal brand") having a particle diameter of several millimeters in a coal blend is large and that, even in the case where the particle diameter of a single coal brand is small, in the case where the coal blend is not sufficiently mixed and where moisture content is more than 6 [mass %], there is an increase in the mass fraction of pseudo-particles having a particle diameter of 1 [mm] or more, which results in a decrease in homogeneity on the order of millimeters.

Also, the present inventors found that determining some properties of a coal blend which satisfy specific conditions is effective as a method for quantitatively evaluating the homogeneity on the order of millimeters of a coal blend. For example, it is possible to quantitatively evaluate homogeneity by determining a change in sulfur concentration in a coal blend.

As described above, the present inventors clarified what kind of criterion should be used in order to evaluate the homogeneity on the order of millimeters of a coal blend. In addition, the present inventors reached a conclusion that, by stirring and mixing a coal blend by using a mixer having a capability for satisfying such a criterion, it is possible to prevent a decrease in coke strength even in the case where the moisture content of the coal blend is more than 6 [mass %].

The present disclosure has been completed on the basis of the knowledge described above. Exemplary disclosed embodiments include as follows.

[1] A method for manufacturing coke including: a preparing step of blending two or more coal brands to prepare a coal blend; a stirring and mixing step of stirring and mixing the coal blend which has been prepared in the preparing step to disintegrate at least a part of pseudo-particles that have been formed by agglomeration of coal particles in the coal blend; and a carbonizing step of charging the stirred and mixed coal blend into a coke oven to carbonize the stirred and mixed coal blend, wherein a mixing apparatus is used in the stirring and mixing step, the mixing apparatus having a capability of controlling degree of mixing of the coal blend to be 0.85 or more at 60 seconds after start of a mixing operation, the degree of mixing being calculated by a following equation (1):

$$\text{degree of mixing} = (\sigma C_0 - \sigma C)/(\sigma C_0 - \sigma Cf) \quad (1)$$

where the degree of mixing is a value calculated from the standard deviations of characteristic values which are respectively determined for samples taken from the stirred and mixed coal blend, $\sigma C_0$ denotes the standard deviation of characteristic values when mixing is not performed at all, $\sigma Cf$ denotes the standard deviation of characteristic values when mixing has been completely performed, $\sigma C$ denotes the standard deviation of characteristic values of the samples taken.

[2] A method for manufacturing coke including: a preparing step of blending two or more coal brands to prepare a coal blend; a stirring and mixing step of stirring and mixing the coal blend which has been prepared in the preparing step to disintegrate at least a part of pseudo-particles that have been formed by agglomeration of coal particles in the coal blend; and a carbonizing step of charging the stirred and mixed coal blend into a coke oven to carbonize the stirred and mixed coal blend, wherein a mixing apparatus is used in the stirring and mixing step, the mixing apparatus having a capability of controlling degree of mixing of the coal blend to be 0.85 or more at 60 seconds after start of a mixing operation, the degree of mixing being calculated by a following equation (2):

$$\text{degree of mixing} = (\sigma TS_0 - \sigma TS)/(\sigma TS_0 - \sigma TSf) \quad (2)$$

where the degree of mixing is a value calculated from the standard deviations of sulfur concentrations which are respectively determined for the samples taken from the stirred and mixed coal blend, $\sigma TS_0$ denotes the standard deviation of sulfur concentrations when mixing is not performed at all, $\sigma TSf$ denotes the standard deviation of sulfur concentrations when mixing has been completely performed, $\sigma TS$ denotes the standard deviation of sulfur concentrations of the samples taken.

[3] The method according to item [1] or [2] above, wherein the coal blend is stirred and mixed in the stirring and mixing step so that the degree of mixing is 0.85 or more.

[4] The method according to item [1] or [3] above, wherein the coal blend has a value of $(\sigma C_0 - \sigma Cf)/\text{Cave}$ of 0.40 or more, where Cave denotes an average value of the determined characteristic values.

[5] The method according to item [2] or [3] above, wherein the coal blend has a value of $(\sigma TS_0 - \sigma TSf)/\text{TSave}$ of 0.40 or more, where TSave denotes an average value of the determined sulfur concentrations.

[6] The method according to any one of items [1], [3], and [4] above, wherein the degree of mixing is a value calculated from the standard deviations of characteristic values which are respectively determined for the samples having a weight of 2 g or less, the sample being taken from plural positions of the stirred and mixed coal blend.

[7] The method according to any one of items [2], [3], and [5] above, wherein the degree of mixing is a value calculated from the standard deviations of sulfur concentration which are respectively determined for the samples having a weight of 2 g or less, the sample being taken from plural positions of the stirred and mixed coal blend.

[8] The method according to any one of items [1] to [7] above, wherein the preparing step includes a step of pulverizing two or more coal brands before blending the two or more coal brands.

[9] The method according to any one of items [1] to [8] above, wherein the preparing step includes a step of controlling the moisture contents of the two or more coal brands.

[10] The method according to any one of items [1] to [9] above, including performing the stirring and mixing step to a coal blend having a moisture content of 6 mass % or more.

[11] Coke manufactured by the method according to any one of items [1] to [10] above.

[12] A method for evaluating homogeneity of a coal blend when coke is manufactured by the method according to any one of items [1], [3], [4], [6], and [8] to [10] above, the method including steps of: taking samples from any positions of a coal blend before and after a stirring and mixing step; determining the characteristic value of each of the samples; calculating a degree of mixing from the standard deviations of characteristic values which are respectively determined for the samples having a value of $(\sigma C_0 - \sigma Cf)/\text{Cave}$ of 0.40 or more; and evaluating the homogeneity of the coal blend on the basis of the degree of mixing which is calculated by equation (3):

$$\text{degree of mixing} = (\sigma C_0 - \sigma C)/(\sigma C_0 \sigma Cf) \quad (3)$$

where $\sigma C_0$ denotes the standard deviation of characteristic values when mixing is not performed at all, $\sigma Cf$ denotes the standard deviation of characteristic values when mixing has been completely performed, $\sigma C$ denotes the standard deviation of characteristic values in an any state of mixing, and Cave denotes the average value of the determined characteristic values.

[13] The method according to item [12] above, wherein the characteristic values are respectively the sulfur concentrations the samples.

[14] The method according to item [12] or [13] above, wherein the characteristic values are respectively determined for the samples having a weight of 2 g or less, the sample being taken from plural positions of the coal blend before and after the stirring and mixing step.

[15] The method according to item [13] or [14] above, wherein the sulfur concentration is determined by using a carbon-sulfur analyzer.

[16] The method according to any one of items [12] to [15] above, wherein a sensitizer is mixed into the coal blend and then the coal blend stirred.

[17] The method according to item [16] above, wherein the sensitizer is at least one of oil coke, coal-tar pitch, and asphalt pitch.

Advantageous Effects

According to the present disclosure, it is possible to obtain coke having a high strength and excellent extrusion capability from a coke oven. In addition, it is possible to evaluate the homogeneity of a coal blend.

DESCRIPTION OF EMBODIMENTS

Figure 1:
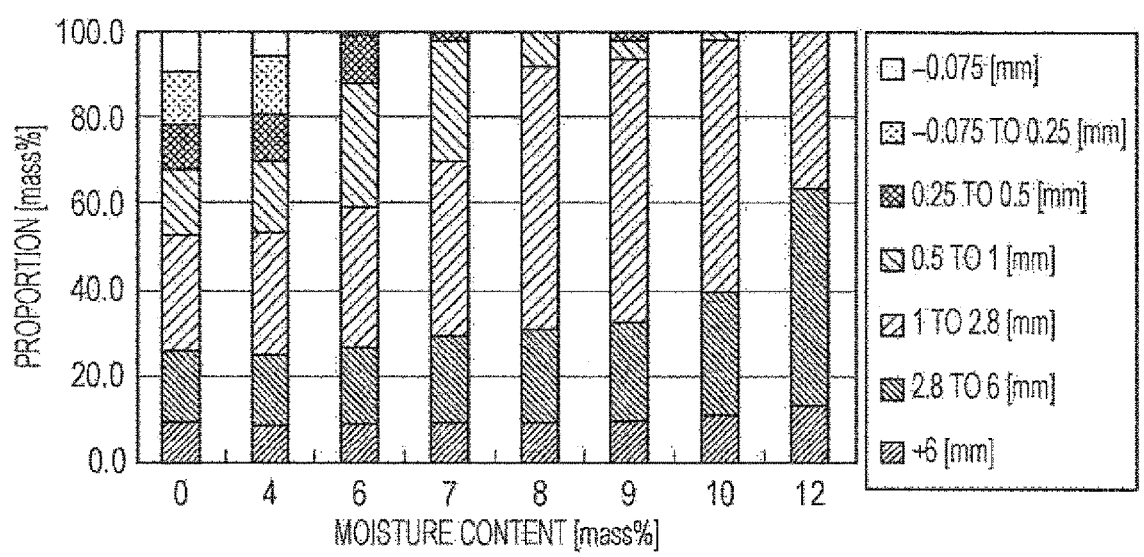
FIG. 1 is a diagram illustrating the relationship between the moisture content of a coal blend and particle size distribution.

Hereafter, the process of investigations through which the present disclosure was conceived will be described in detail, and then an exemplary embodiment of the present disclosure will be described.

[Relationship Between the Homogeneity of a Coal Blend and Coke Strength]

First, the present inventors conducted investigations regarding the relationship between the moisture content of a coal blend and the state of pseudo-particles formed (Experiment 1), and then conducted investigations regarding the influence of the formation of pseudo-particles on the homogeneity of a coal blend and coke strength (Experiments 2 and 3).

Experiment 1

A coal blend having general properties was used as an experimental sample. The general properties are ones for manufacturing metallurgical coke. Table 1 represents the properties (mean maximum reflectance Ro [%], Gieseler maximum fluidity log MF [log ddpm], volatile matter content VM [mass %], and ash matter content Ash [mass %]) and blending ratios [mass %] of four kinds of single coal brands (coal A through coal D) of which the coal blend was composed. Table 2 represents a weighted average according to the blending ratios regarding each of properties of the coal blend. Mean maximum reflectance was determined in accordance with JIS M 8816. Gieseler maximum fluidity was determined in accordance with JIS M 8801. Volatile and ash matter contents were determined in accordance with JIS M 8812 and the contents were on a dry basis.

TABLE 1

| Coal | Ro [%] | log MF [log ddpm] | VM [mass %] | Ash [mass %] | Blending Ratio [%] |
|---|---|---|---|---|---|
| Coal A | 1.21 | 1.20 | 22.2 | 7.1 | 25 |
| Coal B | 0.89 | 2.79 | 29.3 | 8.5 | 45 |
| Coal C | 0.96 | 2.85 | 27.4 | 9.6 | 20 |
| Coal D | 0.92 | 3.97 | 35.5 | 7.0 | 10 |

TABLE 2

| | |
|---|---|
| Weighted Average Ro [%] | 0.99 |
| Weighted Average log MF [log ddpm] | 2.52 |
| Weighted Average VM [mass %] | 27.8 |
| Weighted Average Ash [mass %] | 8.2 |

The coal blend was pulverized and prepared so as to have a particle size distribution simulating a practical operation (3 [mm] or less: 75[%], more than 3 [mm] and 6 [mm] or less: 15[%], and more than 6 [mm]: 10[%], in terms of mass % on a dry basis). A method for preparing coal blends having homogeneous moisture content involves: heating the coal blend to a temperature of 107 [° C.] so as to have a moisture content of 0 [mass %]; thereafter adding water; and leaving the samples untouched for 24 hours. The coal blends were prepared by the method, the coal blends having eight kinds of moisture contents (0, 4, 6, 7, 8, 9, 10, and 12 in terms of [mass %]). Subsequently, the coal blends were sieved by using a sieve-shaking machine with a constant impact being repeatedly applied for five minutes, and then particle size distribution was determined. In an ordinary determination of the particle size distribution of coal, sieve analysis is performed after a coal sample is dried so that pseudo-particles are broken. In contrast, in the present experiment, performing sieve analysis with the moisture content of coal being maintained makes it possible to determine the particle size distribution of pseudo-particles.

Table 3 represents the determination results of particle size distribution for each of the moisture contents of a coal blend. FIG. 1 illustrates the relationship between the moisture content of a coal blend and particle size distribution.

As Table 3 and FIG. 1 indicate, in the case where the moisture content of a coal blend was 4 [mass %] or less, the particle size distribution was not substantially different from the initial particle size distribution (in the case of a moisture content of 0 [mass %]). In contrast, in the case where the moisture content of a coal blend was more than around 6 [mass %], there was a marked increase in the mass proportion of particles in particular having a large particle diameter of 1 [mm] or more. From the results of the observation of the particles having a large particle diameter of 1 [mm] or more by using an optical microscope, since there were a large number of pseudo-particles, it was confirmed that the formation of pseudo-particles progressed in the case where the moisture content of a coal blend was more than around 6 [mass %] and that such pseudo-particles were not broken even by the impact applied in the sieve-shaking process.

TABLE 3

| | Weight Fraction of Particle Size Class [mass %] | | | | | | |
|---|---|---|---|---|---|---|---|
| Moisture Content [mass %] | more than 6 mm | more than 2.8 mm and 6 mm or less | more than 1.0 mm and 2.8 mm or less | more than 0.5 mm and 1.0 mm or less | more than 0.25 mm and 0.5 mm or less | more than 0.075 mm and 0.25 mm or less | 0.075 mm or less |
| 0 | 9.9 | 16.4 | 26.6 | 15.2 | 10.1 | 12.6 | 9.2 |
| 4 | 9.0 | 16.5 | 28.2 | 16.9 | 10.6 | 13.1 | 5.7 |
| 6 | 9.3 | 18.1 | 32.4 | 28.5 | 11.3 | 0.6 | 0.0 |
| 7 | 9.6 | 20.1 | 40.3 | 27.8 | 2.1 | 0.1 | 0.0 |
| 8 | 9.7 | 21.9 | 60.4 | 8.0 | 0.0 | 0.0 | 0.0 |
| 9 | 10.4 | 23.0 | 60.1 | 5.0 | 0.0 | 1.5 | 0.0 |
| 10 | 11.6 | 28.5 | 58.1 | 1.7 | 0.0 | 0.0 | 0.0 |
| 12 | 13.7 | 50.3 | 36.0 | 0.0 | 0.0 | 0.0 | 0.0 |

Experiment 2

In order to investigate the influence of the formation of pseudo-particles on the homogeneity of a coal blend and coke strength, by controlling the moisture content of each of coal A through coal D which were used in Experiment 1 to be 3, 4, 6, 8, and 10 [mass %] in advance, pseudo-particles were formed. These were charged into a drum mixer which mainly involves convective mixing and subjected to mixing for 60 seconds in order to obtain coal blends having the blending ratios given in Table 1. By performing a visual test, it was clarified that there was almost no change in the particle size distribution of pseudo-particles between before and after the mixing process. Subsequently, in order to compensate for the shortage, water was added to the coal blends by performing spraying so that the moisture content of the coal blends was 10 [mass %], and the coal blends were then left untouched for 24 hours in order to obtain homogeneous moisture content.

The strength of coke obtained from the coal blends as described above was evaluated through the following procedures.

By filling 17.1 [kg] of each of the coal blends to a carbonizing vessel so that the bulk density (based on dry weight) was 725 [kg/m$^3$], by carbonizing the coal blend with a weight of 10 [kg] being placed on the top of the carbonizing vessel in an electric furnace having a furnace wall temperature of 1050 [° C.] for 6 hours, by removing the carbonizing vessel from the furnace, and then by cooling the carbonizing vessel with nitrogen gas, coke was obtained.

The strength of the obtained coke was evaluated in accordance with the drum strength test method prescribed in JIS K 2151. By determining the mass fraction of coke having a particle diameter of 15 [mm] or more after the coke had been rotated 150 times at a rotating speed of 15 [rpm], and by calculating the ratio of the mass fraction to that before the rotation, the ratio multiplied by 100 was defined as drum index DI (150/15) [-].

Subsequently, clearance was evaluated through the following procedures.

Figure 2:
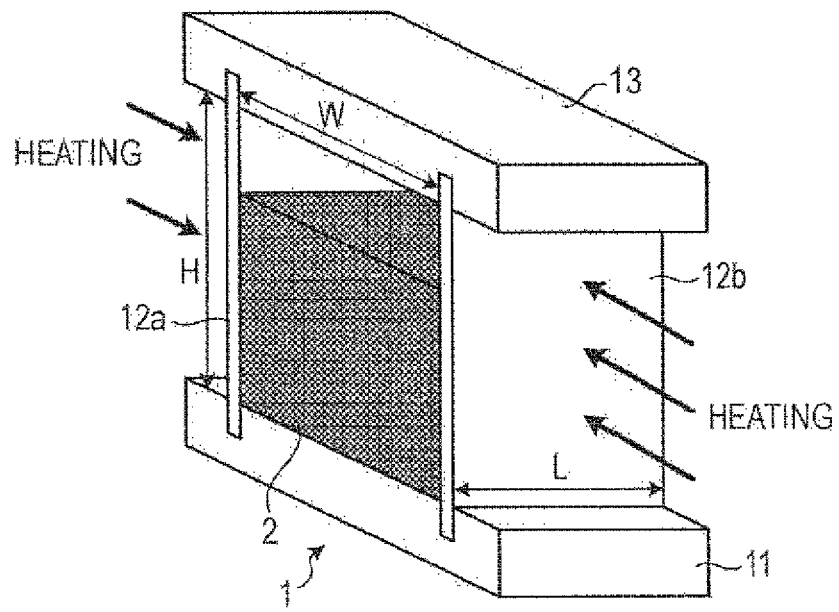
FIG. 2 is a schematic diagram illustrating a method for evaluating clearance.
Figure 2:
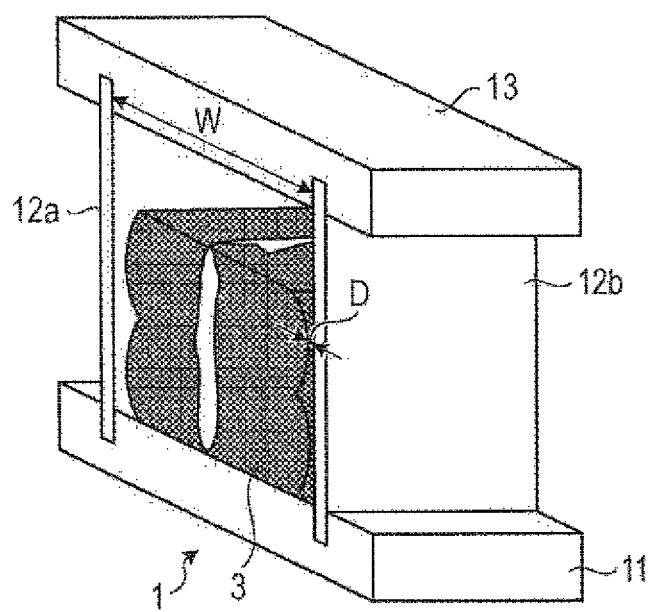

FIGS. 2(a) and (b) are schematic diagrams illustrating a small simulation retort 1 for evaluating clearance. This small simulation retort 1 had a length L of 114 [mm], a width W of 190 [mm], a height H of 120 [mm], a bottom panel 11 composed of bricks, a pair of side panels 12a and 12b composed of metal which stood up from the bottom panel 11, and a top panel 13 composed of bricks which was placed on the top of the pair of side panels 12a and 12b. By filling the small simulation retort with 2.244 [kg] of coal blend 2 so that the bulk density (based on dry weight) was 775 [kg/m$^3$], by carbonizing the coal blend in an electric furnace having a furnace wall temperature of 1050 [° C.] for 4 hours and 20 minutes, by removing the retort from the furnace, and then by cooling the retort with nitrogen gas, a coke cake was obtained. A gap D between the side surface of the obtained coke cake 3 and each of the side panels 12a and 12b was determined by using a laser distance meter. By calculating the average value of the gap D on each of the sides, the sum of the gaps on both sides was defined as a clearance.

Moisture contents before a mixing step and the determined results of coke strength and clearance are given in Table 4. In addition, FIG. 3 illustrates the relationship between the moisture content before a mixing step and the coke strength.

TABLE 4

| Mixing-Step Moisture Content [%] | DI (150/15) [—] | Clearance [mm] |
|---|---|---|
| 3 | 83.0 | 13.8 |
| 4 | 83.1 | 13.7 |
| 6 | 83.1 | 13.7 |
| 8 | 82.5 | 13.7 |
| 10 | 82.0 | 13.6 |

Figure 3:
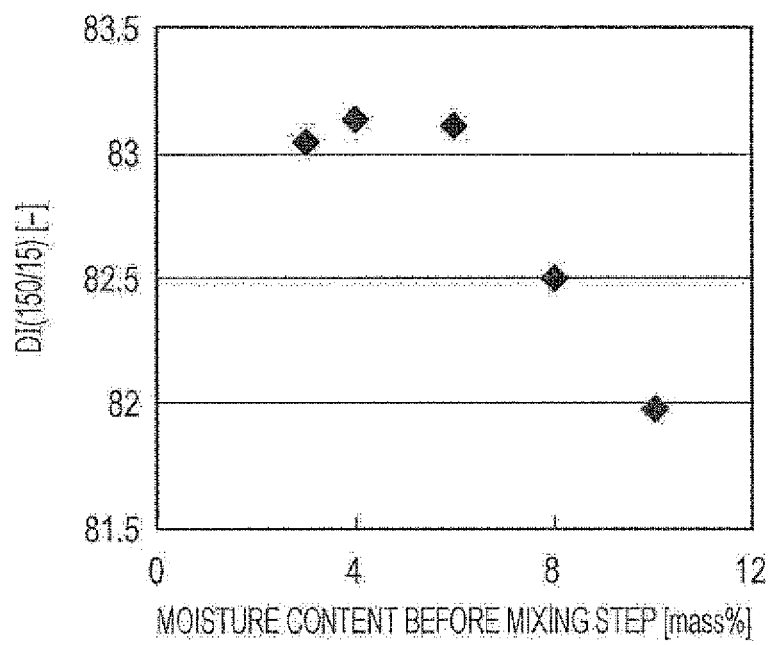
FIG. 3 is a diagram illustrating the relationship between the moisture content of a single coal brand before a mixing step and coke strength.

As Table 4 and FIG. 3 indicate that there was a sharp decrease in coke strength in the case where the moisture content before a mixing step was more than 6 [mass %], although the coke strength was 83.0 or more and there was almost no change in coke strength in the case where the moisture content before a mixing step was 6 [mass %] or less. In contrast, the clearance was almost constant independently of the moisture content before a mixing step.

The inventors of the present disclosure consider that there was a sharp decrease in coke strength in the case where the moisture content before a mixing step was more than 6 [mass %] for the following reason. As FIG. 1 illustrates, in the case where the moisture content of a coal blend is more than 6 [mass %], there is an increase in the mass fraction of pseudo-particles having a particle diameter of 1 [mm] or more. Also, in the case of a single coal brand, the formation of pseudo-particles progresses in the case where the moisture content is more than 6 [mass %]. It is presumed that, in the case where these pseudo-particles remain indisintegrated in a stirring and mixing step, a significantly inhomogeneous coal blend is formed. It is considered that in the case of coke which is obtained by carbonizing such a coal blend, since a difference in, for example, thermoplasticity among pseudo-particles causes large defects, fracturing tends to occur due to the defects. Accordingly, it is difficult to achieve a high strength.

Figure 4:
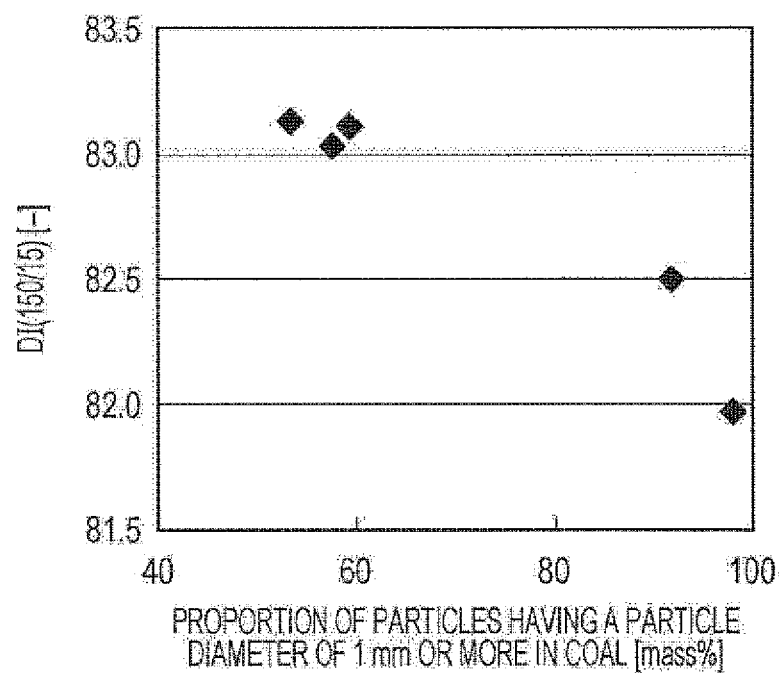
FIG. 4 is a diagram illustrating the relationship between the mass fraction of particles having a particle diameter of 1 [mm] or more in coal and coke strength.
Figure 5:
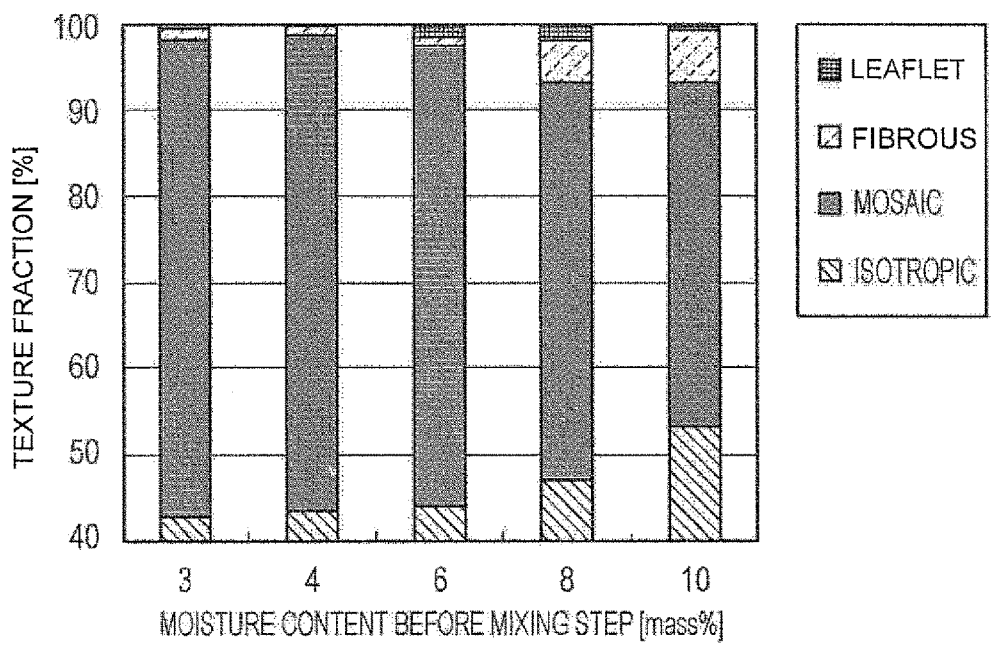
FIG. 5 is a diagram illustrating the relationship between the moisture content of a single coal brand before a mixing step and the evaluation results of an optical texture of coke.

In order to verify the presumption described above, the mass fractions of pseudo-particles having a particle diameter of 1 [mm] or more in the coal blends used in FIG. 3 to determine coke strength were determined. FIG. 4 illustrates the results. In addition, the structure of the obtained coke was observed by using an optical microscope. The characteristic of the coke structure was classified into four categories, that is, "leaflet", "fibrous", "mosaic", and "isotropic", and the proportions of the respective categorized structures were determined. FIG. 5 illustrates the results.

As FIG. 4 indicates, it was clarified that, in the case of a coal blend having a low coke strength of 82.5 or 82.0, the mass fraction of pseudo-particles having a particle diameter of 1 [mm] or more was higher than in the case of coal blends having a coke strength of 83.0 or more. In addition, as FIG. 5 indicates, in the case where the moisture content before a mixing step is more than 6 [mass %], there was a decrease in the proportion of a homogeneous mosaic structure, and there was an increase in the proportions of an isotropic structure and an acicular structure.

As described above, in the case where the moisture content before a mixing step is more than 6 [mass %], since the inhomogeneous structure of coke including a large number of defects therein is formed due to the formation of pseudo-particles, there is a decrease in strength. Therefore, the present inventors considered that it is possible to increase coke strength if pseudo-particles in a coal blend are disintegrated. Here, the reason why the clearance was almost constant independently of the moisture content before a mixing step in Table 4 is considered to be because the moisture content was controlled to be 10% after a blending step.

[Degree of Mixing of a Coal Blend]

On the basis of the results described above, the present inventors conducted additional investigations. As a result, the present inventors focus on the degree of stirring and mixing of a coal blend to find that it is possible to express the disintegrated level of pseudo-particles in a coal blend in terms of the degree of mixing of the coal blend. The present inventors find that the degree of mixing can be quantitatively expressed and used as an index by using the characteristic value of a coal blend for a method for evaluating the degree of mixing of a coal blend and by determining a variation in the characteristic value among samples before and after a stirring and mixing step.

As an example of a method for evaluating the degree of mixing of a coal blend, Non Patent Literature 2 discloses the results of the evaluation of the degree of mixing in the pretreatment process of a coal blend involving using a drum mixer. The degree of mixing is a general index for quantifying the homogeneity of powder and is defined by some equations, and, in any of the definition equations, by using a desired amount of powder under consideration as a population, by taking plural samples from the population, and by determining a characteristic value of each of the samples such as concentration, density, or moisture content, the degree of mixing is calculated on the basis of a variation (such as variance, standard deviation, or coefficient of variation) in the characteristic value among the samples. In Non Patent Literature 2, by adding a radio isotope as a tracer, the degree of mixing defined by equation (4) below is evaluated.

[Math. 4]

$$M' = \frac{CV_1^2 - CV^2}{CV_1^2 - CV_0^2} \times 100 \tag{4}$$

Here, M' denotes the degree of mixing (%), $CV_0$ denotes the coefficient of variation (=standard deviation/average value) of tracer concentration in a complete state of mixing, $CV_1$ denotes the coefficient of variation of tracer concentration in a reference state of mixing, and CV denotes the coefficient of variation of tracer concentration in some state of mixing.

As this definition equation indicates, the degree of mixing M' is an index which approaches 100% as a state of mixing approaches a complete state of mixing, that is, as homogeneity increases and which, conversely, approaches 0% as a state of mixing approaches a reference state. In Non Patent Literature 2, by taking a sample in an amount (about 300 g) corresponding to the increment shovel in accordance with JIS M 8811-30 as a single sample and by determining the tracer concentration of the sample, the degree of mixing is evaluated on the basis of equation (4). The bulk density of coal varies depending on moisture content and particle size, and, in the case of general coke making, the bulk density is about 0.65 g/cm³ to 0.85 g/cm³. That is, in the case where the mass of a sample is about 300 g, the volume of the sample is about 350 cm³ to 450 cm³, that is, corresponds to a cube having a side length of about 7 cm to 8 cm. That is, it can be said that the degree of mixing according to Non Patent Literature 2 is an index for evaluating the homogeneity of a comparatively large order, that is, of about 7 cm to 8 cm.

However, in the case of the method according to Non Patent Literature 2, it is not possible to evaluate a change in the degree of mixing corresponding to the disintegrated level of pseudo-particles having a particle size illustrated in FIG. 1. Neither information regarding the relationship between the degree of mixing and coke strength nor information regarding homogeneity on the order of millimeters which is considered to have a correlation with coke strength is disclosed.

Therefore, the present inventors conducted investigations regarding various characteristic values of coal and the conditions to be satisfied by the characteristic values in order to evaluate homogeneity on the order of millimeters. As a result thereof, the present inventors found that it is preferable to express the degree of mixing by equation (1) below.

degree of mixing=$(\sigma C_0 - \sigma C)/(\sigma C_0 - \sigma C_f)$ (1)

Here, the degree of mixing is a value calculated from the standard deviation of characteristic values which are respectively determined for the samples taken from any positions of a coal blend before and after a stirring and mixing step. $\sigma C_0$ denotes the standard deviation of characteristic values when mixing is not entirely performed. $\sigma Cf$ denotes the standard deviation of characteristic values when mixing has been completely performed. $\sigma C$ denotes the standard deviation of characteristic values in a state of mixing.

Here, the term "the standard deviation of characteristic values in a state of mixing" refers to the standard deviation of characteristic values which are respectively determined for the samples taken in a certain state of mixing. Although, for example, the constituent chemical elements in coal or the physical or chemical property may be used as the characteristic value, it is preferable to use a property whose value varies depending on coal brand. For example, the content of a particular chemical element in coal, the content of ash matter, the content of metal in ash matter, reflectance, the content of a constituent structure, or thermoplasticity may be used.

Hereafter, an example in which the sulfur concentration in coal is used as the characteristic value will be described.

The degree of mixing can be quantitatively expressed and used as an index by using sulfur contained in a coal blend for a method for evaluating the degree of mixing of a coal blend and by determining a variation in sulfur concentration among samples.

First, by using sulfur concentration in coal as a characteristic value, the degree of mixing was calculated. Subsequently, in order to determine a preferable range of the degree of stirring and mixing in terms of the degree of mixing, the proportion of disintegrating of pseudo-particles having a particle diameter of 1 [mm] or more was calculated and defined as the disintegrated level, and the relationship between the disintegrated level and the degree of mixing was clarified.

First, the definition of the degree of mixing and an example of a method for determining the degree of mixing will be described. Hereafter, the determining procedures and the evaluating method will be described in detail. The present experiment example was performed as follows.

(1) At 60 seconds after the start of stable stirring, 15 samples each having a weight of about 100 g are taken from about 8 tons of a coal blend.

(2) From each of the samples, one sample having a specified weight (for example, 1 g) which does not contain particles having a large particle diameter of more than 6 mm is selected.

(3) By determining the sulfur concentration of each of the selected samples, the value is defined as the representative value of the corresponding sample having a weight of about 100 g. By calculating the standard deviation of the representative values of the 15 samples having a weight of about 100 g, the concentrations of which are determined by the same method, the degree of mixing defined by equation (2) is calculated.

$$\text{degree of mixing} = (\sigma TS_0 - \sigma TS)/(\sigma TS_0 - \sigma TSf) \quad (2)$$

Here, $\sigma TS_0$ denotes the standard deviation of sulfur concentrations when mixing is not entirely performed, $\sigma TSf$ denotes the standard deviation of sulfur concentrations when mixing has been completely performed, and $\sigma TS$ denotes the standard deviation of sulfur concentrations of the samples taken.

It is possible to theoretically calculate variations in characteristic values among samples when mixing has not been performed. The procedures will be described below. A case is considered where N samples are taken at random from a coal blend when mixing has not been performed. At this time, the probability of taking each of the constituent single coal brands of the coal blend is equivalent to the blending ratio of the corresponding single coal brand. For example, when the characteristic value of coal 1 is defined as $C_1$ and the blending ratio of the coal is defined as $x_1$, in the case where ideal random sampling is realized, the number of samples having a characteristic value of $C_1$ is $Nx_1$. Therefore, the standard deviation of the characteristic value when mixing has not been performed is calculated by equation (5) below. In the case where the sulfur concentration in coal is used as the characteristic value, $\sigma TS_0$ described above is derived.

[Math. 5]

$$\sigma C_0 = \sqrt{\sum_{i=1}^{n} \frac{(Nx_i(\overline{C} - C_i)^2)}{N}} \quad (5)$$

$$= \sqrt{\sum_{i=1}^{n} (x_i(\overline{C} - C_i)^2)}$$

Here, $\sigma C_0$ denotes the standard deviation of characteristic values when mixing is not performed at all, i denotes the identification number of each of constituent single coal brands of a coal blend, n denotes the total number of constituent single coal brands of a coal blend, $x_1$ denotes the blending ratio of a constituent single coal brand i contained in the coal blend, $\overline{C}$ denotes the weighted average value of the characteristic values of the coal blend which is calculated by equation (6) below, and $C_i$ denotes the characteristic value of a constituent single coal brand i contained in the coal blend.

$$\overline{C} = \sum_{i=1}^{n} x_i C_i \quad (6)$$

In addition, the standard deviation of characteristic values (for example, sulfur concentration) when mixing has been completely performed is estimated as the square root of the unbiased variant which is derived by performing analysis plural times on well-mixed finely pulverized coal. This estimation is based on the principle that it is possible to estimate the standard deviation of a population as the square root of the unbiased variant among samples taken from the population. Since it is considered that the standard deviation of characteristic values when mixing has been completely performed is an analysis error (that is, a standard deviation which is derived by performing analysis plural times on the completely same sample), an already-known analysis error may be used. In addition, as a simplified method, $\sigma Cf$ ($\sigma TSf$ in the example described above) may be assigned a value of 0. Since this simplified method is mathematically reasonable in the case of an analysis with sufficiently high accuracy, and since $\sigma Cf$ takes a constant value, this simplified method may be used as a simplified method of operation control.

In addition, when the degree of mixing is derived, it is preferable that the degree of mixing be a value calculated from the standard deviation of a characteristic value which is determined for each of the samples having a weight of 2 g or less taken from plural positions of a stirred and mixed coal blend. By taking each sample having a weight of 2 g or less from plural positions, since there is a large difference in strength between the case where the degree of mixing is 0.85 or more and the case where the degree of mixing is less than 0.85, it is possible to realize the effect of the present disclosure to a higher degree.

The analysis of sulfur concentration was performed as follows by using carbon-sulfur analyzer EMIA-810 manufactured by HORIBA, Ltd. A sample weighing 0.1 g was placed on a combustion boat and covered with 0.7 g of alumina powder. By charging the combustion boat into an electric furnace at a temperature of 1450° C., by burning the coal in an oxygen gas stream, and by integrating the concentration of sulfur dioxide generated for 160 seconds, the concentration of sulfur dioxide was converted to the sulfur concentration in a coal blend. Here, in order to evaluate the degree of stirring and mixing of a coal blend, an element mapping method using an electron probe micro analyzer (EPMA) may be used. An element mapping method using an EPMA is a method in which a mapping image is derived by detecting the characteristic X-ray of sulfur induced by an electron beam. Although it is possible to evaluate the state of dispersion by performing image analysis on the mapping image of sulfur, there is a disadvantage in that the method requires high techniques including one for sample preparation and a long time to perform determination. On the other hand, a method using a carbon-sulfur analyzer, which requires short time to analyze one sample, and with which analysis is easily performed by using a small amount of sample, is more preferable. Also, there is an advantage in that, since the detection sensitivity of sulfur is very high, the expensive sensitizer described below is not needed.

Here, in order to evaluate the degree of mixing, determination may be performed by adding a material having a characteristic value different from the average value as a sensitizer. For example, determination may be performed by adding a material, as a sensitizer, having a characteristic value 1.5 times or more the weighted average value calculated by equation (6) above in an amount of more than 0.001 times and of less than 1 times the total amount of a coal blend. As long as a sensitizer does not have substantive negative effect on coke strength, coke may be manufactured by performing carbonization with the sensitizer remaining added. For example, although sulfur is a chemical element which is originally contained in coal, a sensitizer having a large sulfur content may be added in order to perform analysis with a higher sensitivity. It is particularly preferable to use, as a sensitizer, oil coke, which is blended as an alternative to coal, or a binder such as coal tar pitch or asphalt pitch, which is added to a coal blend in order to improve coke strength in the coke manufacturing process.

In addition, it is preferable to use a coal blend having a value of $(\sigma C_0 - \sigma Cf)/Cave$ of 0.40 or more. In order to increase the evaluation precision of the degree of mixing, it is preferable that $\sigma C_0$, which is the standard deviation of characteristic values when mixing has not been performed, be large. From the results of the investigations regarding various conditions conducted by the present inventors, it was found that it is preferable to use a coal blend having a characteristic value with which $(\sigma C_0 - \sigma Cf)/Cave$ is 0.40 or more, or more preferably 0.55 or more. Here Cave is the average value of determined characteristic values. As Cave, the average value of the characteristic values of the constituent coal brands of a coal blend weighted by the blending ratios of the constituent coal brands may be used. Also, in the case where $\sigma Cf$ is assigned a value of 0, a characteristic value with which $\sigma C_0/Cave$ is 0.42 or more, or preferably 0.57 or more, may be used.

Hereafter, the definition of the disintegrated level and an example of a method for measuring the disintegrated level will be described.

(1) Coal to which a powder fluorescent paint (FX-305 manufactured by SINLOIHI. CO. LTD) is applied is used as a tracer. This fluorescent paint is characterized by emitting light under ultraviolet irradiation.

(2) By adding this tracer to a coal blend so that the area fraction of particles having a particle diameter of 1 [mm] or more is about 5[%], by controlling moisture content to be 10 [mass %], a stirring and mixing operation is performed. (3) The photograph of this coal blend is obtained by using a digital camera under ultraviolet irradiation. Since the tracer yields fluorescence in the obtained photograph, by setting appropriate threshold values of, for example, luminance and brightness in order to extract only tracer particles, the particle diameter thereof is determined. Here, the particle diameter of the tracer particle may be defined as the average value of diameters which connect two points on the circumference of the extracted tracer particle, which pass through the center of gravity, and which are determined at intervals of 2 [°]. Also, the particle diameter of the tracer particle may be defined as a circle-equivalent diameter which is derived by performing image analysis on a photograph obtained by using a digital camera.

(4) The disintegrated level is calculated by substituting the determined particle diameter after a stirring and mixing operation into equation (7) below.

$$\text{disintegrated level} = 1 - A/A_0 \quad (7)$$

Here, in equation (7), parameter A denotes the area fraction of particles having a particle diameter of 1 [mm] or more after a stirring and mixing operation, and $A_0$ denotes the initial area fraction of particles having a particle diameter of 1 [mm] or more (about 5[%]). That as the disintegrating of pseudo-particles progresses, the disintegrated level approaches 1.

Experiment 3

The present inventors evaluated the disintegrated level and the degree of mixing by using five kinds of mixers of different types in terms of stirring and mixing method and capability and by performing a stirring and mixing treatment for a certain time on a coal blend to which a sensitizer was added and whose moisture content was controlled to be 10 [mass %]. By taking 15 samples each having a weight of 1 g from a coal blend, and by determining the sulfur concentration of each of the samples, the degree of mixing was calculated from the determined values. Among the five kinds of mixers, mixer A was a drum mixer which was widely used in conventional coke plants and which mainly involves convective mixing. Mixers C through E were mixers of a shear-mixing type, and mixer B was a mixer in which convex mixing and shear mixing occurred in combination. Here, the term "convex mixing" refers to mixing mainly involving the convection and diffusion of a sample, and the term "shear mixing" refers to mixing involving shearing, collision, abrasion, and so forth of a sample.

Figure 6:
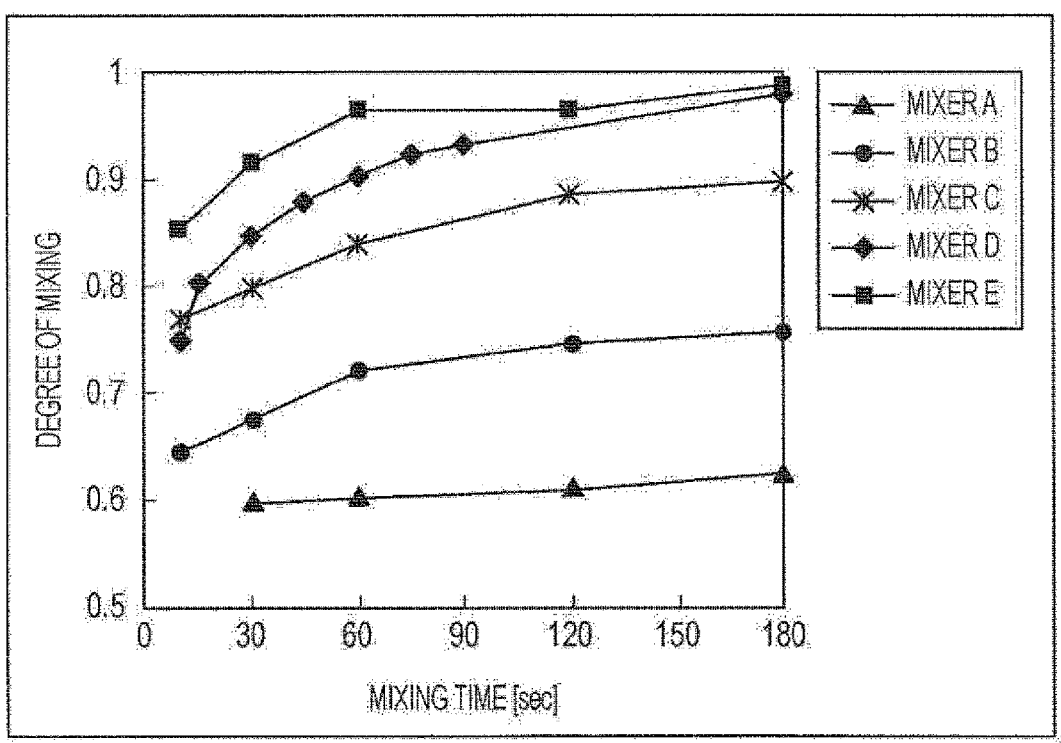
FIG. 6 is a diagram illustrating the relationship between the stirring and mixing time of a mixer and the degree of mixing.
Figure 7:
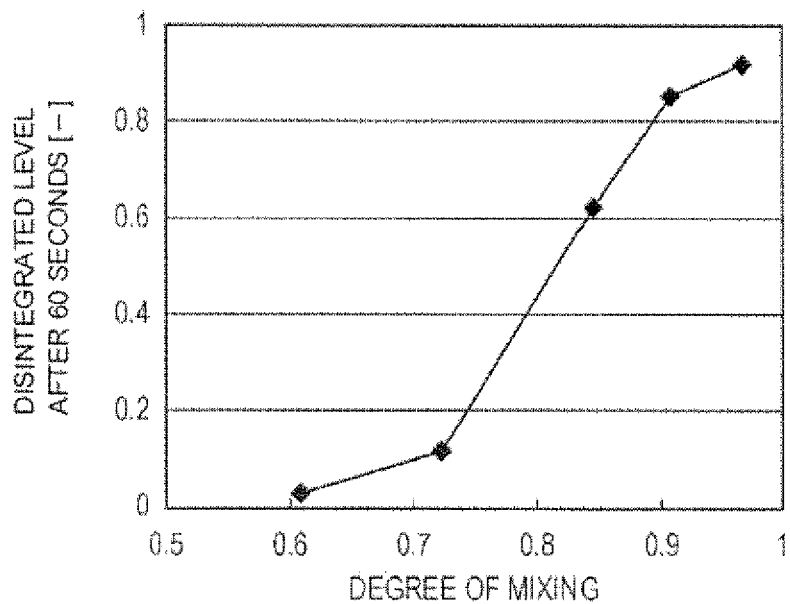
FIG. 7 is a diagram illustrating the relationship between the degree of mixing after 60 seconds and the disintegrated level.

FIG. 6 illustrates the relationship between the stirring and mixing time of each of the mixers and the degree of mixing. In addition, FIG. 7 illustrates the relationship between the degree of mixing after 60 seconds of stirring and the disintegrated level. In FIG. 7, in the ascending order of the degree of mixing and the disintegrated level, the points of mixers A, B, C, D, and E are arranged.

As FIG. 7 indicates, it is clarified that the disintegrated level largely changes in a range corresponding to a degree of mixing of 0.75 to 0.85. That is, in the case where the degree of mixing of a coal blend is 0.85 or more, or preferably 0.9 or more, pseudo-particles are disintegrated, and it is possible to manufacture coke having homogeneity (on the order of millimeters). As described above, in the present disclosure, by taking samples from any positions of a coal blend before and after a stirring and mixing step, by determining the characteristic value of each of the samples, and by calculating the degree of mixing from the standard deviation of the characteristic value among the samples by using equation (1) above, the homogeneity of the coal blend is evaluated in terms of the degree of mixing. For example, by taking samples from desired positions of a coal blend before and after a stirring and mixing step, by determining the sulfur concentration of each of the samples, and by calculating the degree of mixing from the standard deviation of sulfur concentration among the samples by using equation (2) above, the homogeneity of the coal blend is evaluated in terms of the degree of mixing. In addition, when coke is manufactured, stirring and mixing are performed so that the degree of mixing is 0.85 or more. This is based on the fact that, as described in the EXAMPLES below, from the results of the investigations regarding the relationship between the degree of mixing of a coal blend and the strength of coke which is manufactured by carbonizing the coal blend, it is possible to obtain coke having sufficiently high strength in the case where the degree of mixing of the coal blend is 0.85 or more. Examples of a method for stirring and mixing include one using a mixing apparatus having a capability of controlling the degree of mixing of a coal blend to be 0.85 or more at 60 seconds after the start of the mixing operation.

As FIG. 6 indicates, since the degree of mixing of a coal blend after 60 seconds is 0.85 or more in the case of mixers C through E, it is clarified that it is preferable to use mixers C though E, which mainly involve shear mixing, in order to manufacture coke in the present disclosure. In contrast, in the case of drum mixer A, which is used in conventional coke plants, and which mainly involves convex mixing, pseudo-particles are not substantially disintegrated. In the case of mixer B, in which convex mixing and shear mixing occur in combination, although there was an increase in the degree of mixing to about 0.75 in the case where the stirring and mixing time was more than 60 seconds, which means that the disintegrating of pseudo-particles progressed compared with in the case of mixer A, the degree of mixing of a coal blend after 60 seconds was less than 0.85. Therefore, even in the case of a mixer of a convex-mixing type or a mixer of a type in which convex mixing and shear mixing occur in combination, as long as it is possible to perform stirring and mixing so that the degree of mixing of a coal blend after 60 seconds is 0.85 or more, or preferably 0.9 or more, such a mixer may be used for manufacturing coke in the present disclosure.

Examples of a mixer in a practical operation include one of a batch type and one of a continuous type in accordance with method of treatment. A treatment time is equivalent to a stirring and mixing time in the case of a mixer of a batch type, and an average retention time is equivalent to a stirring and mixing time in the case of a mixer of a continuous type. In the case of a mixer of any type, as long as the degree of mixing is 0.85 or more, or preferably 0.9 or more, when the degree of mixing of a coal blend is determined after a retention time of 60 seconds, such a mixer may be used as a preferable apparatus. Since it is necessary to treat coal in a huge amount of several hundred [t/h] or more for manufacturing coke, it is preferable that a mixer used in a coke-making line be a mixer of a continuous type having a high treatment capacity. In addition, since a coke-making process involves a pulverizing step, a mixing step, a drying step (including a partially drying step), and so forth, a coal blend is mixed in a treatment in each of the steps and in transportation steps, there is a tendency for the coal blend to be homogenized. Therefore, it is preferable that a stirring and mixing treatment using a mixer be performed as shortly as possible before the coal blend is charged into a coke oven if it is performed after a mixing step from the viewpoint of homogeneity and efficiency.

Here, it is not necessary to vaporize all the water in coal in a drying step, and examples of a drying step include a partially drying step in which moisture content is decreased and a moisture-controlling step. In addition, a coal blend may contain additives such as binders, oils, powder coke, oil coke, resins, and wastes.

[Method for Manufacturing Coke]

A coal blend is prepared by blending two or more of coal brands. Subsequently, by stirring and mixing the coal blend which has been prepared in a preparing step, at least a part of pseudo-particles which has been formed in the coal blend as a result of coal particles adhering to each other is disintegrated. At this time, a mixing apparatus having a capability of controlling the degree of mixing of the coal blend, which is calculated by equation (1) above, to be 0.85 or more at 60 seconds after the start of the mixing operation is used. Moreover, the coal blend which has been subjected to a stirring and mixing step is charged into a coke oven and carbonized. As described above, coke is manufactured.

Here, when a coal blend is prepared, it is preferable that the two or more coal brands be pulverized before the two or more coal brands are blended. By thus pulverizing the two or more of coal brands before the two or more coal brands are blended, there is an increase in the effect of increasing coke strength as a result of stirring and mixing.

In addition, when a stirring and mixing treatment is performed, it is preferable that a stirring and mixing treatment is performed on a coal blend having a moisture content of 6 mass % or more from the viewpoint of clearance. In addition, in the case where the moisture content of a coal blend is more than 6 mass % when a stirring and mixing treatment is performed, there is an increase in the effect of increasing coke strength as a result of performing a stirring and mixing treatment so that the degree of mixing is 0.85 or more compared with coke strength in the case where a stirring and mixing treatment is not performed or where a stirring and mixing treatment is insufficiently performed. Therefore, it is more preferable that stirring and mixing be performed on a coal blend having a moisture content of more than 6 mass %.

Example 1

By adding water to four kinds of single coal brands (coal A through coal D) having the properties given in Table 1, and by leaving the single coal brands untouched for 24 hours in order to obtain homogeneous moisture content, the moisture content was controlled to be 3 [mass %] to 14 [mass %]. By using the mixers A through E described above involving different types of stirring and mixing functions, these single coal brands were subjected to stirring and mixing for 60 seconds in order to prepare coal blends having blending ratios given in Table 1. By filling a carbonizing vessel with 17.1 [kg] of each of the prepared coal blends so that the bulk density (based on dry weight) was 725 [kg/m$^3$], by carbonizing the coal blend with a weight of 10 [kg] being placed on the top of the carbonizing vessel in an electric furnace having a furnace wall temperature of 1050 [° C.] for 6 hours, by removing the carbonizing vessel from the furnace, and then by cooling the carbonizing vessel with nitrogen gas, coke was obtained. The drum index DI (150/15) and clearance of the obtained coke were determined. The method for determining drum index DI (150/15) was as described above. Clearance was determined as follows.

By filling a small simulation retort for determining clearance with 2.244 [kg] of the coal blend having a bulk density (based on dry weight) of 775 [kg/m$^3$], the coal blend was carbonized in an electric furnace having a furnace wall temperature of 1050 [° C.] for 4 hours and 20 minutes. The retort was removed from the furnace and cooled with nitrogen gas. A gap between the side surface of the obtained coke cake and each of the side panels on the right and left sides was determined by using a laser distance meter. By calculating the average value of the gap on each of the sides, the sum of the gaps on both sides was defined as a clearance.

The moisture content when mixing was performed, drum index DI (150/15), and clearance of each of the samples are given in Table 5.

method according to the present disclosure be used in the case where a coal blend having a high moisture content is carbonized.

Example 2

The present inventors, by evaluating the degree of mixing under various material conditions, investigated the relationship between the determined degree of mixing and coke strength.

Sample size influences the detection sensitivity of the degree of mixing. That is, the smaller the sample size, the larger the influence of particles having a characteristic value different from the average value of a coal blend. In contrast, in the case where a sample size is large, since particles having various characteristic values are contained in the sample, there is a decrease in a variation due to averaged characteristic value. Therefore, the smaller the sample size, the higher the detection sensitivity of the degree of mixing. On the other hand, it is necessary to use a certain amount of sample in order to analyze a characteristic value, and there is an increase in analysis error in the case of a small sample size. The present inventors conducted investigations regard-

TABLE 5

| Mixing-Step | Mixer A (Comparative Example 1) | | Mixer B (Comparative Example 2) | | Mixer C (Example 1) | | Mixer D (Example 2) | | Mixer E (Example 3) | |
|---|---|---|---|---|---|---|---|---|---|---|
| Moisture Content [%] | DI (150/15) [—] | Clearance [mm] | DI (150/15) [—] | Clearance [mm] | DI (150/15) [—] | Clearance [mm] | DI (150/15) [—] | Clearance [mm] | DI (150/15) [—] | Clearance [mm] |
| 3 | 83.0 | 13.8 | 83.1 | 13.8 | 83.2 | 13.8 | 83.2 | 13.8 | 83.2 | 13.8 |
| 4 | 83.1 | 13.7 | 83.1 | 13.8 | 83.2 | 13.8 | 83.2 | 13.8 | 83.2 | 13.8 |
| 6 | 83.1 | 13.7 | 83.1 | 13.7 | 83.1 | 13.8 | 83.2 | 13.8 | 83.2 | 13.8 |
| 8 | 82.5 | 13.7 | 82.7 | 13.7 | 83.0 | 13.7 | 83.1 | 13.7 | 83.1 | 13.8 |
| 10 | 82.0 | 13.6 | 82.0 | 13.7 | 82.7 | 13.7 | 83.0 | 13.7 | 83.1 | 13.8 |
| 14 | 81.0 | 13.6 | 81.2 | 13.6 | 83.0 | 13.7 | 83.0 | 13.7 | 83.0 | 13.7 |

As Table 5 indicates, it is clarified that, by performing stirring and mixing by using any one of the mixers C, D, and E having a capability of controlling the degree of mixing of a coal blend after 60 seconds of stirring and mixing to be 0.85 or more, or preferably 0.9 or more, since the disintegrating of pseudo-particles progressed, it was possible to manufacture coke excellent in terms of both coke strength and clearance even in the case where moisture content was 6 [mass %] or more. That is, in the case where mixer A or B was used, coke strength achieved was much smaller in the case where moisture content was more than 6 mass % than in the case where moisture content was 6 mass %. On the contrary, by using mixer C, D, or E with which the degree of mixing of a coal blend after 60 seconds of stirring and mixing was 0.85 or more, coke strength which was achieved in the case where moisture content was more than 6 mass % is almost equal to that in the case where moisture content was 3 mass % to 6 mass %, which means that the effect of increasing coke strength as a result of stirring was large. Here, although no difference in determined clearance resulting from variations in the moisture content is observed in Table 5 because carbonization was performed with a constant bulk density in the testing method described above, it is known that, in a practical operation, in the case where moisture content is high, since there is a decrease in the bulk density of coal charged into the carbonization chamber of a coke oven on a dry basis, there is an increase in the amount of shrinking. Therefore, it is particularly preferable that the ing how sample size influences the degree of mixing and the detection sensitivity of coke strength by performing a carbonization test.

By using a coal blend (base coal blend) which is practically used in a commercial coke oven and coal blends which were prepared by adding delayed oil coke to the base coal blend as a sensitizer in an amount of 0.1% to 50%, the coal blends were subjected to pulverization, blending, and moisture control. Subsequently, the coal blends having a weight of 300 kg were made into coal blends having various degrees of mixing by using mixers having various stirring capabilities and by performing stirring for various periods of time. The properties (mean maximum reflectance Ro [%], Gieseler maximum fluidity log MF [log ddpm], volatile matter content VM [mass %], ash matter content Ash [mass %], and total sulfur content (TS) [mass %]) of single coal brands (coal E through coal T) and delayed oil coke which were contained in the coal blends used in the test are given in Table 6, and the average properties of the base coal blend are given in table 7.

TABLE 6

| Brand | Ro [%] | log MF [ddpm/log] | VM [% d.b.] | Ash [% d.b.] | TS [% d.b.] |
|---|---|---|---|---|---|
| Coal E | 1.11 | 3.08 | 24.9 | 9.2 | 0.55 |
| Coal F | 1.20 | 1.55 | 21.3 | 7.2 | 0.42 |

TABLE 6-continued

| Brand | Ro [%] | log MF [ddpm/log] | VM [% d.b.] | Ash [% d.b.] | TS [% d.b.] |
|---|---|---|---|---|---|
| Coal G | 1.22 | 0.60 | 21.2 | 8.2 | 0.29 |
| Coal H | 0.97 | 3.26 | 27.5 | 11.2 | 0.44 |
| Coal I | 1.10 | 4.23 | 27.7 | 8.4 | 0.80 |
| Coal J | 1.14 | 1.04 | 23.0 | 12.0 | 0.34 |
| Coal K | 1.19 | 2.40 | 22.0 | 9.1 | 0.42 |
| Coal L | 1.00 | 2.63 | 27.3 | 7.9 | 0.47 |
| Coal M | 0.74 | 4.33 | 38.8 | 9.2 | 0.55 |
| Coal N | 0.98 | 2.55 | 25.9 | 9.4 | 0.44 |
| Coal O | 1.01 | 3.16 | 27.6 | 10.7 | 0.98 |
| Coal P | 1.00 | 2.63 | 27.3 | 7.9 | 0.47 |
| Coal Q | 1.00 | 1.67 | 25.4 | 9.5 | 0.41 |
| Coal R | 0.92 | 0.90 | 25.3 | 9.1 | 0.39 |
| Coal S | 0.75 | 2.24 | 37.3 | 9.9 | 0.67 |
| Coal T | 1.30 | 0.30 | 18.7 | 10.7 | 0.40 |
| Delayed Oil Coke | 2.33 | 0.00 | 12.2 | 0.3 | 3.13 |

TABLE 7

| | |
|---|---|
| Weighted Average Ro [%] | 1.01 |
| Weighted Average log MF [ddpm/log] | 2.67 |
| Weighted Average VM [% d.b.] | 27.1 |
| Weighted Average Ash [% d.b.] | 9.2 |
| Weighted Average TS [% d.b.] | 0.5 |

Coke strength was evaluated through the following procedures. A laboratory furnace having a capacity of ¼ tons was used to carbonize each of the coal blends. By charging about 200 [kg] of a coal blend into the furnace through free fall, by carbonizing the coal blend in an electric furnace having a furnace wall temperature of 950 [° C.] for 23 hours, by then removing the sample from the furnace, and by cooling the sample with nitrogen gas, coke was obtained. Regarding the strength of the obtained coke, in accordance with the drum strength test method prescribed in JIS K 2151, by determining the mass fraction of coke having a particle diameter of 15 [mm] or more after the coke had been rotated 150 times at a rotating speed of 15 [rpm], and by calculating the ratio of the mass fraction to that before the rotation, the ratio multiplied by 100 was defined as drum index DI (150/15).

Regarding the degree of mixing of the coal blend, by taking 15 samples having a specified sample size, by determining total sulfur content in accordance with JIS M 8813, the degree of mixing was calculated by equation (1) above. Here, $\sigma C_0$ of coal blend was 0.18 mass % for the base coal blend and 0.20 mass % to 1.31 mass % for the coal blends containing delayed oil coke, and $(\sigma C_0 - \sigma Cf)/Cave$ was 0.33 for the base coal blend and 0.36 to 1.00 for the coal blends containing delayed oil coke. In addition, $\sigma Cf$ was 0.008 mass % in any case.

Figure 8:
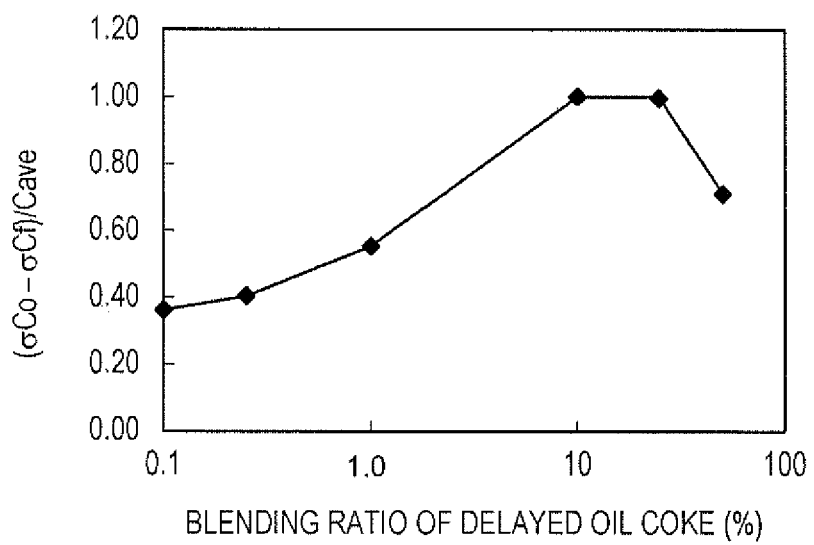
FIG. 8 is a diagram illustrating the relationship between the blending ratio of delayed oil coke and $(\sigma C_0 - \sigma Cf)/Cave$.

FIG. 8 illustrates the relationship between the blending ratio of delayed oil coke and $(\sigma C_0 - \sigma Cf)/Cave$. As FIG. 8 indicates, it is clarified that $(\sigma C_0 - \sigma Cf)/Cave$ has a maximal value when plotted against the blending ratio of a sensitizer.

Figure 9:
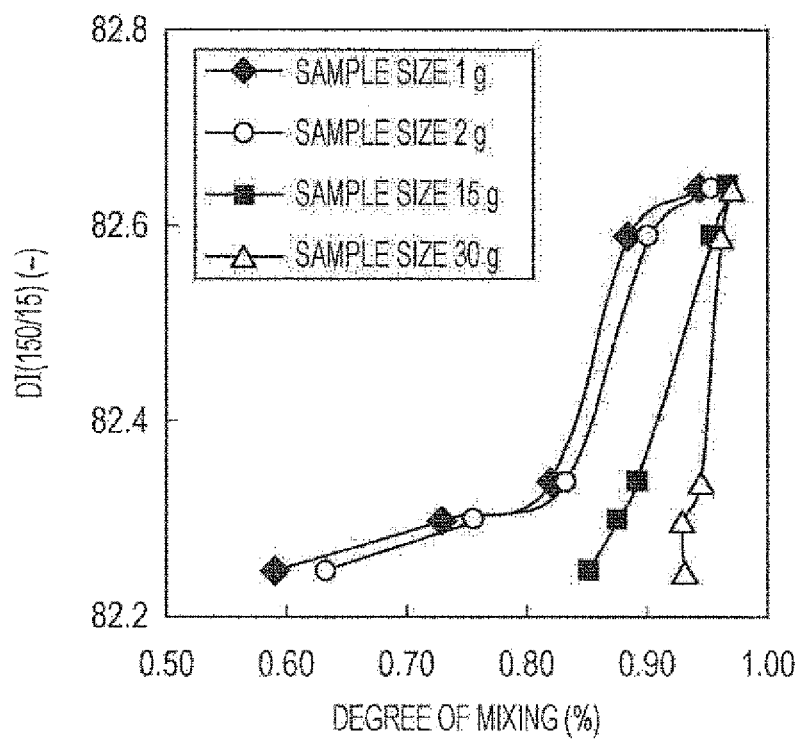
FIG. 9 is a diagram illustrating the relationship between the degree of mixing of a coal blend and coke strength.

Subsequently, by using a coal blend having a value of $(\sigma C_0 - \sigma Cf)/Cave$ of 1.00 which was obtained by adding delayed oil coke to the base coal blend, and by determining the degrees of mixing for various sample sizes, the relationship between the determined degree of mixing and the strength of coke which was manufactured by carbonizing the coal blend was investigated. The results are illustrated in FIG. 9. The points indicating the same strength represent the coke which was manufactured from the same coal blend. As FIG. 9 indicates, it is clarified that, since the determined degree of mixing of the same coal blend varies depending on sample size, plural points are plotted for the same value of strength. It is clarified that, the larger the sample size, the smaller the difference between the maximum and minimum values of the determined degree of mixing, which results in a decrease in the detection sensitivity of the degree of mixing. It is clarified that, in the case where the sample size was 15 g or less, there is a tendency for coke strength to improve with improving degree of mixing. Therefore, it is clarified that, in order to detect the degree of mixing, it is preferable that the sample size be 15 g or less, or more preferably 2 g or less. It is possible to determine the lower limit of the sample size from the viewpoint of a method for analyzing a characteristic value, and it is preferable that the lower limit be 0.1 g or more.

As FIG. 9 indicates, it is clarified that, in the case where the sample size was 2 g or less, there was a large difference in coke strength between the case where the degree of mixing was 0.85 or more and the case where the degree of mixing was less than 0.85. It is clarified that it is preferable that stirring be performed so that the degree of mixing is 0.85 or more in order to maintain a high level of coke strength.

Example 3

The influence of $(\sigma C_0 - \sigma Cf)/Cave$ on the determined value of the degree of mixing was investigated. By adding delayed oil coke to the base coal blend in various amounts, coal blends having various values of $(\sigma C_0 - \sigma Cf)/Cave$ were prepared. Subsequently, by stirring the coal blends by using mixers having various stirring capability, the degree of mixing after stirring was determined with a sample size of 1 g. In Table 8, the degrees of mixing determined after stirring by using mixer B having the highest stirring capability and mixer A having the lowest stirring capability and the difference in the degree of mixing between the two mixers are given.

TABLE 8

| $(\sigma C_0 - \sigma Cf)/Cave$ | Degree of Mixing after Stirring by Using Mixer E | Degree of Mixing after Stirring by Using Mixer A | Difference in Degree of Mixing |
|---|---|---|---|
| 0.33 | 0.96 | 0.93 | 0.03 |
| 0.36 | 0.96 | 0.93 | 0.03 |
| 0.40 | 0.95 | 0.79 | 0.16 |
| 0.55 | 0.95 | 0.71 | 0.24 |
| 1.00 | 0.94 | 0.59 | 0.35 |

As Table 8 indicates, it is clarified that, in the case where $(\sigma C_0 - \sigma Cf)/Cave$ was 0.36 or less, there was almost no difference in the degree of mixing determined after a mixing step between mixers A and E. On the other hand, in the case where $(\sigma C_0 - \sigma Cf)/Cave$ was 0.40 or more, since there was an increase in a difference in the degree of mixing, it was possible to detect a difference in the degree of mixing. From the results described above, it is clarified that it is preferable to use a coal blend having a value of $(\sigma C_0 - \sigma Cf)/Cave$ of 0.40 or more, or more preferably 0.55 or more. Here, at this time, in the case where $(\sigma C_0 - \sigma Cf)/Cave$ was 0.40 or more, coke strength was 82.5 or more for a degree of mixing of 0.85 or more, and coke strength was less than 82.5 for a degree of mixing of less than 0.85.

Example 4

By evaluating the degree of mixing of a mixer used in a practical coke oven with the method according to the present disclosure, coke strength was evaluated. In the final stage of a pretreatment process in a coke-making line, that is immediately before a transportation step through which coal was carried to a coke oven, the mixer was installed. The mixer was of a continuous type and had a capability of controlling the degree of mixing to be 0.85 or more after 60 seconds of a mixing operation (that is, after an average retention time of 60 seconds).

Figure 10:
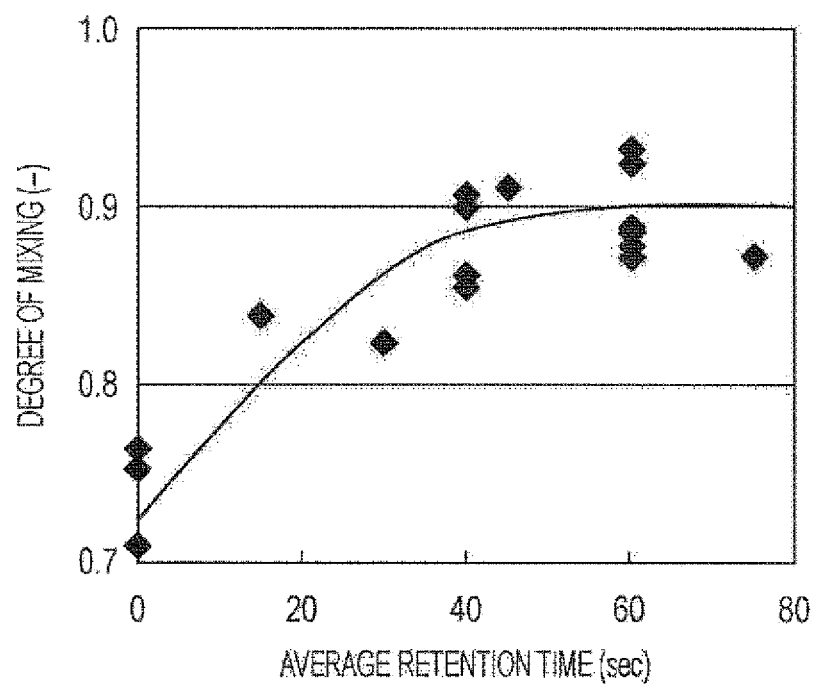
FIG. 10 is a diagram illustrating the relationship between a treating time (average retention time) of a mixer and the degree of mixing of a coal blend.

The change in the degree of mixing of a coal blend according to a treatment time in the mixer was investigated. Total sulfur content prescribed in JIS M 8813 was used as a characteristic value. Here, delayed oil coke was added to the coal blend in an amount of 10%. At that time, $\sigma TS_0$ was 0.98, and $(\sigma TS_0 - \sigma TSf)/TSave$ was 0.99. Each of the populations of the coal blend taken on the belt conveyers on the inlet and exit sides of the mixer had a weight of about 6 tons. By taking plural specimens having a weight of about 1.2 kg from the population by using a sampling shovel in accordance with JIS M 8811-50, and 15 samples having a sample size of about 1 g was taken from each of the specimens. Total sulfur content of each of the samples was determined in accordance with JIS M 8813. The degree of mixing was calculated by equation (2) above. FIG. 10 illustrates the obtained results. As FIG. 10 indicates, it is clarified that, the longer the average retention time in the mixer, the higher the degree of mixing.

Figure 11:
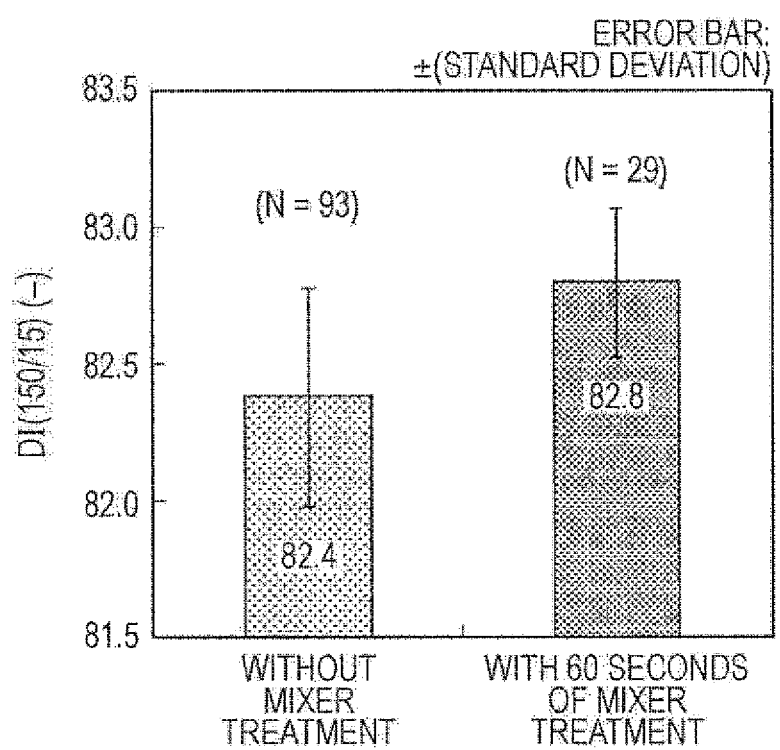
FIG. 11 is a diagram illustrating the relationship between the coke strength derived from a coal blend before a mixer treatment and the coke strength derived from a coal blend after 60 seconds of a mixer treatment (treatment for an average retention time of 60 seconds).

A change in the strength of coke manufactured by using a practical coke oven due to the installed mixer was investigated. FIG. 11 illustrates coke strengths in the case where a treatment using the mixer was not performed (the degree of mixing≈0.74) and in the case where a treatment using the mixer was performed for an average retention time of about 60 seconds (the degree of mixing 0.90%). Here, coke strength was determined every 8 hours during the test period. As FIG. 11 indicates, from the results of t-test with a confidence interval of 95% on both sides, it is clarified that there was an improvement in drum strength due to a stirring treatment using the mixer with a significant difference. In addition, from the results of F-test with a confidence interval of 95% on both sides, it is clarified that there was a decrease in a variation in strength with a significant difference. The reason why there was a decrease in a variation in strength is considered to be because, as a result of installing the mixer, there was an improvement not only in homogeneity on the order of millimeters but also in macro homogeneity.

As described above, by using the degree of mixing evaluated in the present disclosure as an index, and by performing an operation in order to improve the degree of mixing, it is possible to achieve an improvement in coke strength and a decrease in a variation in coke strength.

Although the exemplary embodiments of the present disclosure by the present inventors have been described above, the present disclosure includes, but is not limited to, the descriptions and figures of the present embodiments. That is, other embodiments, working examples, and operational techniques and the like, which are performed on the basis of the present embodiments by those with an ordinary skill in the art are all within the scope of the present disclosure.

REFERENCE SIGNS LIST 1 small simulation retort
2 coal blend
3 coke cake
11 bottom panel
12a, 12b side panel
13 top panel

The invention claimed is:

1. A method for evaluating homogeneity of a coal blend and manufacturing coke comprising:
blending two or more coal brands to prepare the coal blend;
stirring and mixing the coal blend to disintegrate at least a part of pseudo-particles that have been formed by agglomeration of coal particles in the coal blend, wherein a mixing apparatus is used in the stirring and mixing step, the mixing apparatus having a capability of controlling a degree of mixing of the coal blend to be 0.85 or more at 60 seconds after start of a mixing operation, the degree of mixing being calculated by the following equation (1):

$$\text{degree of mixing} = (\sigma C_0 - \sigma C)/(\sigma C_0 - \sigma Cf) \tag{1}$$

where the degree of mixing is a value calculated from the standard deviations of characteristic values which are respectively determined as follows:
$\sigma C_0$ denotes the standard deviation of characteristic values when mixing is not performed at all,
$\sigma Cf = 0$, and
$\sigma C$ denotes the standard deviation of characteristic values of samples taken from the mixed coal blend;
taking samples from any positions of the coal blend before and after the stirring and mixing step;
determining a characteristic value of each of the samples;
calculating the degree of mixing from the standard deviations of characteristic values which are respectively determined for the samples having a value of $(\sigma C_0 - \sigma Cf)/Cave$ of 0.40 or more, where Cave is a weighted average characteristic value of the coal blend;
evaluating the homogeneity of the coal blend on the basis of the degree of mixing which is calculated by the above equation (1); and
charging the stirred and mixed coal blend into a coke oven to carbonize the stirred and mixed coal blend to form the coke.

2. The method according to claim 1, wherein the characteristic values are respectively the sulfur concentrations of the samples.

3. The method according to claim 2, wherein the sulfur concentration is determined by a carbon-sulfur analyzer.

4. The method according to claim 1, wherein the characteristic values are respectively determined for the samples having a weight of from 0.1 g to 2 g, the samples being taken from plural positions of the coal blend before and after the stirring and mixing step.

5. The method according to claim 1, wherein a sensitizer is mixed into the coal blend and then the coal blend is stirred.

6. The method according to claim 5, wherein the sensitizer is at least one of oil coke, coal-tar pitch and asphalt pitch.

* * * * *